United States Patent
Mosleh et al.

(10) Patent No.: US 7,899,910 B1
(45) Date of Patent: Mar. 1, 2011

(54) METHOD AND APPARATUS FOR INTEGRATED COMMUNICATION SERVICES PROVISIONING FOR HEALTH CARE COMMUNITY

(75) Inventors: Ali Mosleh, Marlboro, MA (US); Richard A. Stanley, Wayland, MA (US)

(73) Assignee: Verizon Laboratories Inc., Waltham, MA (US)

( * ) Notice: Subject to any disclaimer, the term of this patent is extended or adjusted under 35 U.S.C. 154(b) by 0 days.

(21) Appl. No.: 09/385,299

(22) Filed: Aug. 30, 1999
(Under 37 CFR 1.47)

(51) Int. Cl.
*G06F 15/16* (2006.01)
(52) U.S. Cl. ........................................................ 709/227
(58) Field of Classification Search .................. 709/313, 709/314, 227, 228; 707/1, 4, 10, 109.1; 705/2, 705/3
See application file for complete search history.

(56) References Cited

U.S. PATENT DOCUMENTS

| | | | | |
|---|---|---|---|---|
| 5,561,446 A | | 10/1996 | Montlick | ...................... 345/173 |
| 5,732,074 A | | 3/1998 | Spaur et al. .................. 370/313 |
| 5,740,231 A | * | 4/1998 | Cohn et al. ................. 379/88.22 |
| 5,761,621 A | * | 6/1998 | Sainton ......................... 455/453 |
| 5,805,666 A | * | 9/1998 | Ishizuka et al. .............. 379/1.01 |
| 5,867,821 A | | 2/1999 | Ballantyne et al. ................ 705/2 |
| 5,924,095 A | * | 7/1999 | White ............................. 707/10 |
| 6,269,402 B1 | * | 7/2001 | Lin et al. ....................... 709/227 |
| 6,334,126 B1 | * | 12/2001 | Nagatomo et al. ................ 707/4 |
| 6,363,434 B1 | * | 3/2002 | Eytchison ..................... 709/313 |
| 6,449,259 B1 | * | 9/2002 | Allain et al. .................. 370/253 |
| 7,130,396 B2 | * | 10/2006 | Rogers et al. ............ 379/106.02 |

\* cited by examiner

*Primary Examiner* — James Trujillo
*Assistant Examiner* — Marc Somers

(57) ABSTRACT

A method and system of accessing an information system using a portable access device is provided. The method includes identifying a communication profile associated with a first network server, attempting, by the portable access device, to establish a communication link between the portable access device and the first network server using communication channel that is selected by the portable access device based on the communication profile, a location of the portable access device with respect to the first network server, a desired quality of the communication link, and a cost of the communication link, attempting to establish the communication link includes using at least a portion of the description information, and capturing data received by the portable access device in a memory located in the portable access device in accordance with a failed attempt to establish the communication link.

42 Claims, 10 Drawing Sheets

METHOD AND APPARATUS FOR INTEGRATED COMMUNICATION SERVICES PROVISIONING FOR HEALTH CARE COMMUNITY

FIELD OF THE INVENTION

The present invention relates to a method and apparatus for the collection and distribution of medical information and more specifically to integrated wireless and wireline computer systems and methods for accessing and maintaining patient medical information.

DESCRIPTION OF THE PRIOR ART

In 1992, total expenditures within the health care industry were estimated to be almost $800 billion. Nearly 20 percent of this amount was consumed in overhead and administrative costs. In addition, 8-12% of the time spent by physicians in patient care was committed to miscellaneous tasks such as error checking, transcription, and re-submission of insurance claims. Nurses spent as much as 18% of their time charting patient information and managing the paper flow inside of a medical facility. Aside from reducing the inordinately large amount of time spent by medical professionals in accomplishing these administrative necessities, it is expected that an improved quality of care, with concomitant savings in costs could result from the increased availability of accurate and timely medical and insurance claim information.

The health care industry has long recognized the need for a computerized medical information system that can maintain comprehensive and current records of each patient's medical status. In fact, health care providers, information system vendors, and state governments have teamed together to plan and build Health Information Networks (HINs) in at least 11 states. Simultaneously, a host of large corporations have constructed proprietary HINs for processing clinical Electronic Data Interchange (EDI) transactions, including both data and images such as x-rays and CAT scans.

The proliferation of the Internet has also played a significant role in the information exchange between different sectors within the health care industry. Hospitals and outpatient clinics have recently began to schedule appointments, order prescription medicine and review test results from Internet and Intranet sites. While it has been possible to successfully implement traditional centralized on-line computer information systems for geographically limited populations within hospitals and other standalone medical facilities, it has not been a simple straight-forward task to scale-up these systems to accommodate larger, dispersed populations, like medical patients in remote outpatient settings or in-transit accident victims in need of emergency medical assistance. The major problems that make the traditional network models unsuitable for these "point-of-care" applications are: (1) inefficient access to needed data; (2) difficulty in maintaining data currency throughout the system; (3) difficulty in establishing/maintaining communication between remote users and a central database; and (4) cost. Further complicating the problem is the sensitive nature of the information typically found in patient medical records, necessitating restricted access in the interest of privacy. For all these reasons, on-line access to this critical information has primarily been limited to the immediate vicinity around hospitals and other stationary care-providing facilities where access to it can be closely monitored.

Another barrier to the implementation of these networks has been the resistance by the practicing medical professionals. Many physicians and nurses are computer-phobic and/or resistant to changing their practice methods. There is industry-wide consensus that physicians will routinely use hospital and office computers only when they become easy to use and provide significant applications that save time, improve productivity and streamline the patient care process.

An additional barrier to the use and operation of a computer-based health care network is the relatively limited number of individuals currently populating these databases, the difficulty of adding people to the database, and the inconvenience experienced by medical professionals, particularly emergency medical technicians (EMT) who must attempt to access and update these databases while simultaneously performing emergency medical procedures. When an EMT arrives at an accident scene, the last thing he/she wants to do is waste time accessing a remote database, determining whether the injured person's medical record is already stored in the database, or performing a series of complicated database manipulation routines to add the person to the database.

These observations suggest that the current health care system could significantly benefit from a computer network that allowed users to share information in a secure setting over a wide geographic area through the use of a portable, user friendly graphical user interface. U.S. Pat. No. 5,867,821 to Ballantyne et al., entitled a "Method and Apparatus for Electronically Accessing and Distributing Personal Health Care Information and Services in Hospitals and Homes" for example, provides an automated system for distribution and administration of medical information in a hospital or at the patient's home. This system utilizes a pen-based computer interfacing with a patient care station located at a hospital or patient home to provide access to a medical information database. To access patient information, a nursing station located in a hospital or other medical facility downloads requested information via a coaxial cable interface to a patient care station located inside a patient's room or at a patient's home. The information is then passed from the patient care station to the portable pen-based computer via wireless communications or broadband IR communications. While the patient care stations of this device provide a powerful interface tool to the computer network, its coaxial cable interface limits its portability and consequently restricts its use by those located outside of the hospital or other similar medical facility. Furthermore, the relatively short effective range of broadband IR communications, limits the pen-based computer's ability to operate in locations too distant (i.e., greater than 100 feet) from a patient care station.

U.S. Pat. No. 5,561,446 to Montlick discloses a method and apparatus for wireless remote information retrieval and pen-based data entry. In this case, a portable pen-based computer is coupled by a wireless network to a host computer which supplies the portable computer with a user-friendly graphical interface such that drawings and graphics can be entered using a stylus on electronic forms and stored on the computer for later retrieval and access by other users. The wireless network includes a plurality of transceivers strategically positioned in a hospital to ensure constant access to the network from anywhere inside the hospital. While this device represents an increase in the distance from which each portable computer can access the computer network (the effective transmission radius of each transceiver is 300-500 feet), it fails to address the requirement of accessing the medical network beyond 500 feet as is routinely the case when a doctor makes a house call or an EMT responds to an accident scene. This system also does not provide an alternative transmission means in the event that the wireless network becomes inoperable.

Finally, U.S. Pat. No. 5,732,074 to Spaur et al. discloses a mobile wireless communication system for exchanging information between remote mobile sites and a centralized database. The system includes a computer terminal with a modem and cellular phone for long distance wireless communication, as well as an RS232 connection, an Ethernet connection and/or a Personal Computer Memory Card International Association (PCMCIA) unit for alternate communication capability. This patent however, does not disclose a capability of the central database to configure the mobile unit to communicate with numerous network servers, thereby avoiding potential bottlenecks when various mobile units attempt to simultaneously access a common network node. The reference also does not disclose the implementation of a user-friendly graphical interface that permits text, drawings and graphics to be entered using a stylus on electronic forms and stored on the computer for later retrieval and access by other users.

There is a need therefore for an improved apparatus and method for providing wireless or wireline access to a medical information computer network via remote computers such that medical professionals can reliably access the network from any location utilizing a user-friendly graphical interface.

SUMMARY OF THE INVENTION

Systems and methods consistent with this invention provide an integrated communication services (ICS) network that permits wireless and wireline data subscribers to share information on a hospital campus using wireless or wireline LANs, or to seamlessly tap into the facility's databases while in transit away from the hospital. The ICS network permits simplified delivery of patient records to medical professionals for the purpose of checking on the status of a patient, updating the patient status, submitting paperwork for insurance claims, or to monitor the effectiveness and costs of various operations and drugs. The ICS network also provides for the real time capture and transmission of patient information (e.g., vital signs) before and after medical incidents, and the development of a global patient profile (GPP) database to monitor trends and effectiveness of various medical treatments, operations and drugs.

One of the key elements of the ICS network is a point of care terminal for accessing the network and retrieving data files. The point of care terminal resembles a clipboard and accepts data entry from a stylus on an electronic pad. For specialized applications, the point of care terminal can also be configured to accept keyboard, bar-code reader, or other inputs. Information can readily be entered graphically or alphanumerically, and can be displayed graphically, in tables, or in any other user-friendly form. The point of care terminal will replace the current clipboard and handwritten paper charts that today are manually generated and physically routed to numerous locations. The automated point of care terminal will also displace the manual data entry system by providing a network-based data capture and retrieval capability. This terminal eliminates re-entry of data at various locations (forms no longer need to be refilled at different departments) and a single copy of a data file can be shared by a number of doctors, laboratories, and nurses. As such, the terminal can save many hours of time for all medical professionals, thereby increasing hospital efficiency. This time can be spent improving patient care, expanding nursing services, and enhancing the skills of members of the medical profession. One of the greatest benefits of the point of care terminal is its ability to communicate with the rest of the ICS network regardless of its location, in a plurality of communication modes. More specifically, the point of care terminal can communicate with the ICS network either via local wireless or wireline LAN, or remote wireless or wireline LAN. The point of care terminal can even operate in a standalone mode by capturing data on-site and then later uploading the data to the ICS network when circumstances permit.

The ICS network is also comprised of a plurality of network servers geographically dispersed throughout a hospital or other similar medical facility. These servers are usually larger and more powerful than point of care terminals with significantly greater storage capabilities. They can be used to access and interface with the central database much the same way that the point of care terminal interfaces with the central database. However, as a result of their size and processing capabilities, they are somewhat stationary and typically located only in controlled medical settings. Network servers, like point of care terminals, are also capable of interfacing with the ICS network via wireless and wireline networks. They additionally provide wireless and wireline interface capabilities to point of care terminals.

A third major component of the ICS network is the integrated communications clearinghouse (ICC) database server. This database and associated server can be located either inside of, or remote from a hospital. It is used as a central storage of communication profile data and patient treatment data for access by medical professionals located at network servers and point of care terminals. Communication profiles are the detailed communication parameters that must be utilized by one network entity wishing to communicate with another network device operating on the ICS network. These communication profiles are downloaded from the ICC database server to network servers and requesting point of care terminals and network servers that wish to communicate with a specific network resource. The ICC database is also comprised of global patient profile (GPP) data. This data consists of the type of data typically found in a patient's medical records. GPP data includes historical treatment data, patient allergies, physical characteristics, etc. Each time a new patient is added to the system, it constructs a patient profile that is then passed to the ICC database server 50 for archival purposes. As a result, whenever the need arises to examine patient data, the file can be downloaded from the ICC to the patient care provider for evaluation.

As stated earlier, the point of care terminal can utilize several available paths in order to deliver data to its destination. This may include existing off-the-shelf PCMCIA-based peripherals such as: a wireless LAN, a standard wired Ethernet LAN, a land line Modem, or wireless wide area networks. The wireless wide area networks may additionally include several data paths such as a circuit switched cellular, or packet based Cellular Digital Packet Data (CDPD). The actual selection of a particular channel will be service-dependent and a function of the user's whereabouts, the desired quality of the connection, and the costs of the connection. One of the elements used to determine the selection of a specific channel for communications, either local or wide area, is the available network and its coverage area. The selection will also depend on the destination server's configuration which may include: in campus wired Ethernet LANs, hospital-wide wireless Ethernet, wide area wireless networks, and Public Switched Telephone Network (PSTN) connections using standard modems. With the point of care terminal, wireless local area networks can be used within a hospital campus by doctors, nurses and other professionals, provided the user stays within the system's coverage. Once a user travels beyond this coverage, wide area wireless links can be utilized to connect the user to the central database. In the event that a user travels to a geographic location that does not support wide area wireless communication, PSTN telephone lines can be used to connect health care providers to the network via an RS232 connection and an internal modem.

Data will be seamlessly provided to a destination network server, regardless of the type of channel used by the point of care terminal. This delivery is managed by a communication process, or ICS module operating on each point of care terminal and network server. The ICS module chooses the most appropriate communication channel and only prompts the user for assistance when necessary. This notification is intended to instruct the user when appropriate, to take the requisite actions in order to complete the communication link (e.g. "please plug in your PCMCIA wireless interface card"). In operation, when a data file needs to be transmitted, the actual delivery path is selected based on criterion programmed into the communication application and the attached available channels.

On the recipient side, if a particular network server is configured to communicate across several different communication networks (i.e., wireless LAN, wired LAN, PSTN, etc.), the data is received without any knowledge of the medium of transmission or the method of communicating utilized by the point of care terminal. In other words the recipient network server receives the information without being aware of the transmitting point of care terminal's type of transport, whether a wireless LAN, a PSTN, or cellular interface. To achieve this effect, the ICS module first determines whether the transmitting point of care terminal and the recipient network server are within the coverage area of the local wireless LAN. If not, the ICS module determines the most efficient communication path that offers the lowest cost with minimum delay to establish the connection. In this fashion, the recipient network server is guaranteed to get the data regardless of the type of channel(s) a transmitting point of care terminal has access to. The system is also usable even when it is out of any service area through data capture. In essence, a medical professional performing house calls could first download relevant patient data from the ICC database, travel to the location of the homebound patient, furnish home health care in the remote area not served by wireless or wireline systems, capture observed patient data in system memory on the remote computer and then update the central database with the recorded information upon their return to the coverage area.

To share data with the computer network, a user at a point of care terminal or network server simply transmits a data file to the ICS network for processing. The ICS module operating on the point of care terminal or the ICS network, scans all the available PCMCIA communication channels and selects the optimum channel to establish the connection. To accomplish this function, the ICS module interfaces with a communications profile database to retrieve communications profile data and other interface parameters of the receiving station. The communications profile database can be stored either on the point of care terminal or on the ICC database server. This storage scheme reduces the number of simultaneous queries to the main database and offers additional reliability to the overall concept. Whenever communications profile data is changed at a local directory (network server), the change will automatically be reported back to the main database and then on to a point of care terminal (if necessary) in order to maintain data integrity.

It is to be understood that both the foregoing general description and the following detailed description are exemplary and explanatory only and are not restrictive of the invention, as claimed.

BRIEF DESCRIPTION OF THE DRAWINGS

The accompanying drawings, that are incorporated in and constitute a part of the specification, illustrate presently preferred embodiments of the invention and, together with the general description given above and the detailed description of the preferred embodiments given below, serve to explain the principles of the invention.

DETAILED DESCRIPTION

Figure 1:
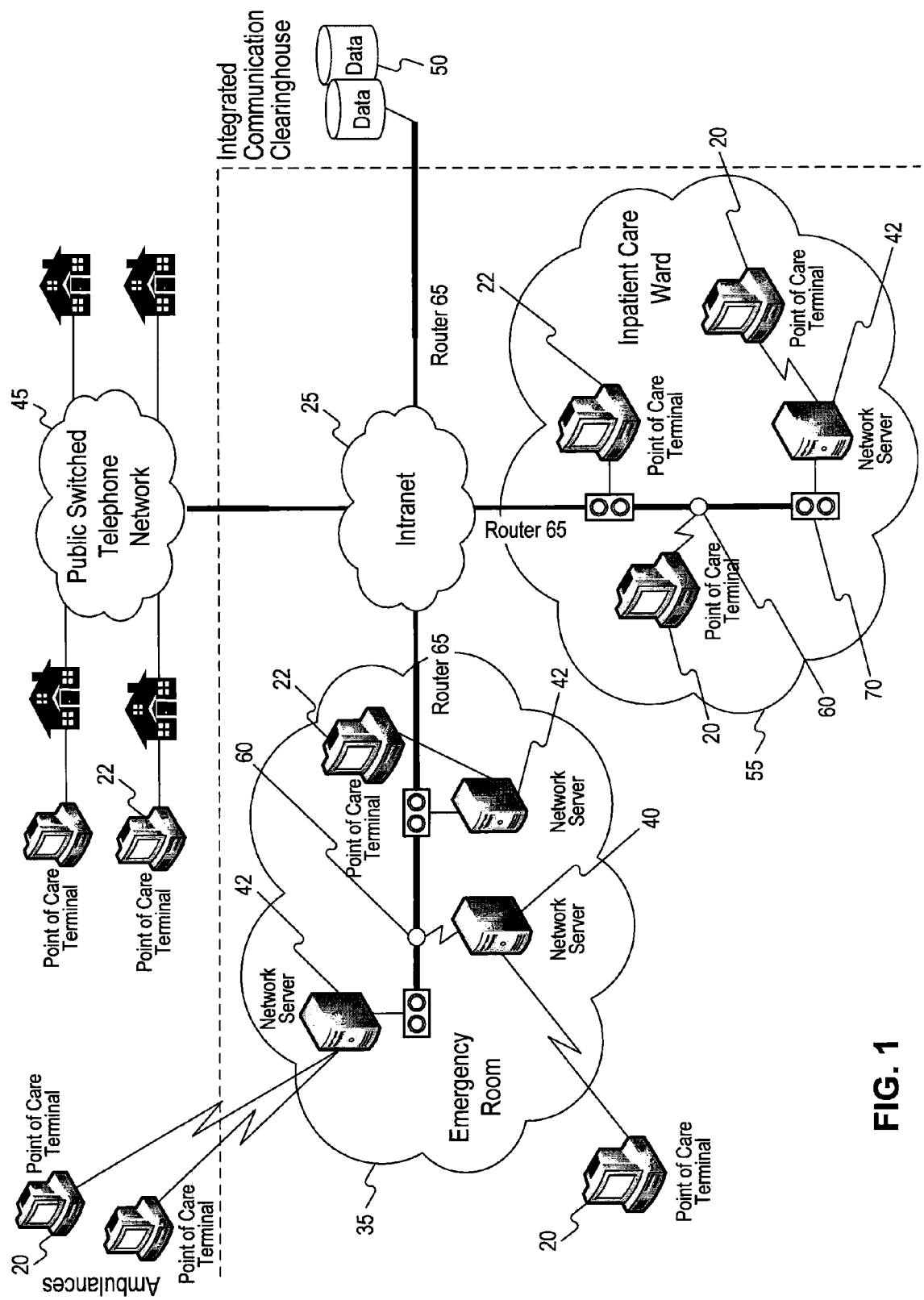
FIG. 1 is a block diagram of a network including an arrangement constructed in accordance with the subject invention for providing an integrated communications services network.

In the following detailed description of the preferred embodiment, reference is made to the accompanying drawings that form a part thereof, and in which is shown by way of illustration a specific embodiment in which the invention may be practiced. This embodiment is described in sufficient detail to enable those skilled in the art to practice the invention and it is to be understood that other embodiments may be utilized and that structural changes may be made without departing from the scope of the present invention. The following detailed description is, therefore, not to be taken in a limited sense.

A system in accordance with the present invention, comprises a plurality of point of care terminals and associated network server computers. The network server computers may be generally similar to the point of care terminals including a central processing unit, display device, multiple transceivers and operator input device. Moreover, it will be appreciated that a point of care terminal may also perform operations described herein as being performed by a network server computer, and similarly a network server computer may also perform operations described herein as being performed by a point of care terminal. The distributed system may comprise any one of a number of types of networks over which client computers and server computers communicate, including local area networks (LANs), wide area networks (WANs), the Internet and any other networks that distribute processing and share data among a plurality of nodes.

Referring now to the drawings, in which like numerals represent like elements throughout the several figures, the present invention will be described.

Referring to first to FIG. 1, an Integrated Communications Services (ICS) network system 10, is comprised of a plurality of interconnected computers and microprocessors hosting a plurality of operating systems. By way of example, the network can be comprised of Pentium™ based microprocessors operating on Windows/NT, UNIX and/or Windows/CE operating systems.

ICS network 10 includes network server computers (40 and 42), point of care terminals (20 and 22) and Integrated Communication Clearinghouse (ICC) database server 50. The ICS network 10 also includes an intranet 25, an emergency room sub-network 35, a PSTN 45, and a inpatient care ward sub-network 55. The servers and terminals are connected to the ICS network 10 via a series of transceivers 60 and 10 Base-T connectors 70. For purposes of illustration, network servers 40 and point of care terminals 20 are depicted as wireless terminals that interface with the ICS network 10 via a network transceiver 60, while network servers 42 and point of care terminals 22 are depicted as wireline terminals that interface with the ICS network 10 via a 10 Base T connector 70 or other similar network cable interface. In reality, all network servers and point of care terminals possess both wireless and wireline capabilities. The hard-wired coupling can either be accomplished through a network interface or via a modem connected to a PSTN 45. Devices coupled to the network via a wireless interface communicate with rest of the network 10 over the airwaves at radio frequencies while devices coupled to the network via a hard-wired interface communicate with the rest of the computer network 10 over a wire or fiber optic medium.

As shown in FIG. 1, ICS network 10 is located inside of a hospital 30 and is connected to the emergency room 35, PSTN 45 and the inpatient care ward 55 by a series of routers 65. While this figure depicts three separate sub-networks, it is understood by those of skill in the art that the number of sub-networks is only limited by the size and complexity of the hospital 30. The items depicted outside of the dotted line are typically located outside of the hospital 30 and those items depicted inside the dotted line are located inside of the hospital 30. The ICC 50 may be located either inside, or outside the hospital 30. Point of care terminals (20 and 22) and network servers (40 and 42) provide the ICS network 10 with a high degree of versatility. For example, as shown in the inpatient care ward 55, patient care terminal 20 is capable of directly interfacing via wireless communication with the ICS network 10 through a wireless transceiver 60. Point of care terminal 20 can also interface via wireless communication with the network ICS 10 through a network server 42. Point of care terminal 22, as shown in the inpatient care ward 55 is capable of directly interfacing via wireline communication with the ICS network 10 through a 10 Base-T connector 70. FIG. 1 also shows the capability of point of care terminals 22 to interface with the PSTN 45 through a telephone jack (not shown) in a patient's home.

The versatility of the ICS network 10 is further evidenced by the capabilities of the network servers (40 and 42) in the emergency room 35. More specifically, network servers (40 and 42) are capable of interfacing with the ICS network 10 via a first wireless or wired interface while simultaneously communicating with point of care terminals across a second wireless or wired interface. As shown in FIG. 1, network server 42 can effectively interface with the ICS network 10 and point of care terminal 22 via a wired interface, and network server 40 can simultaneously interface with the ICS network 10 and point of care terminal 20 via wireless networks. Network server 42 inside of emergency room 35 is also capable of simultaneously communicating with the network ICS 10 and the point of care terminal 22 via a hybrid network. This high degree of flexibility ensures a communication capability under virtually any circumstances.

FIG. 1 shows that regardless of location, point of care terminals 20 and 22 can be connected to the wireless LAN either through a wireless or wired interface. Inside of the hospital the connection to the LAN can be via a wireless transceiver 60 physically coupled to the network or through network server (40 and 42). Outside of the hospital, point of care terminals 20 can be linked to the wireless LAN either through a cellular link, as in the case of the point of care terminals utilized by emergency medical technicians (EMTs) in ambulances. They can also be linked to the wireless network through a modem (not shown) interfacing with the PSTN 45, as in the case of point of care terminals 22 utilized by medical professionals providing home health care. Network servers (40 and 42) located inside of the hospital 30 can likewise communicate with the wireless LAN either through a wired or wireless interface. However, as a result of their relatively large size and backup memory function, they are not routinely utilized outside of the hospital or stationary medical facility environment. Network servers (40 and 42) and point of care terminals (20 and 22) located inside of the hospital 30 are ordinarily utilized by physicians, nurses or other medical specialists typically working inside of a hospital, while point of care terminals (20 and 22) located outside of the hospital 30 can be utilized by any medical professional who is otherwise authorized access to the ICS network 10, but located outside of the hospital.

Figure 2:
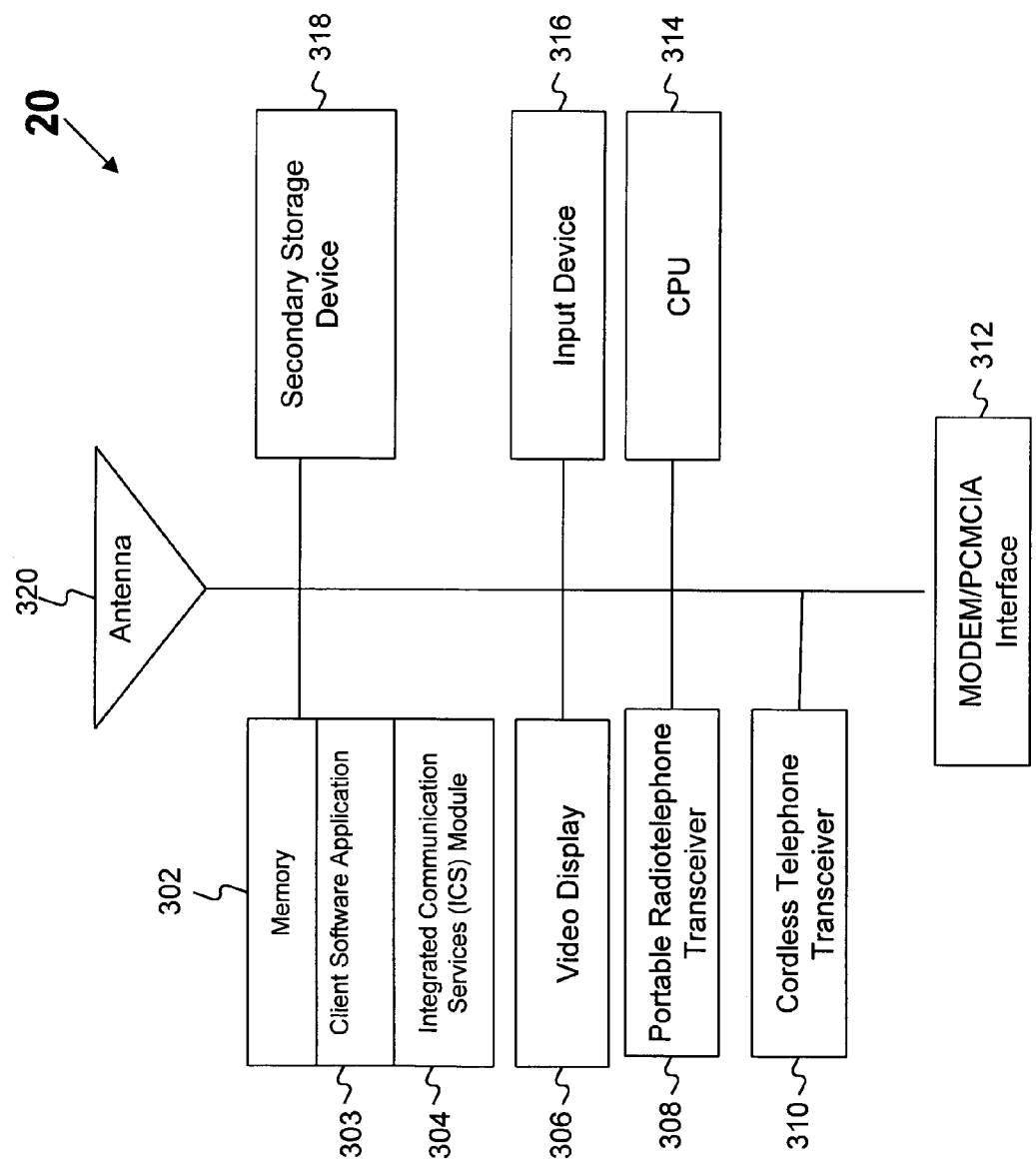
FIG. 2 is a more detailed block diagram of the point of care terminal of FIG. 1.

As shown in FIG. 2, a point of care (POC) terminal includes a memory 302, a client software module 303, a local ICS module 304, a video display 306, a portable radiotelephone transceiver 308, a cordless telephone transceiver 310, a Modem/PCMCIA interface 312, a central processing unit (CPU) 314, an input device 316, a secondary storage 318 and an antenna 320.

Local ICS module 304 provides the point of care terminal with the capability to communicate with network servers (40 and 42) and the ICC database server 50 using several attached communication channels. ICS module 304 evaluates the user's location relative to the wireless Ethernet installed inside of the hospital, and performs the functions necessary to establish the most economical and efficient data communication link based on the user's location. The local ICS module 304 is a collection of the point of care terminal's most frequently used communication profiles, and is most likely a subset of communication profiles stored on the network server (40 and 42) and the ICC database server 50. A more detailed explanation of the operation of the local ICS is provided with reference to FIG. 6.

The portable radiotelephone transceiver 308 performs radiotelephone or cellular type communication and wireless Cordless telephone transceiver 310 performs cordless telephone type communication. Wireless Ethernet-type communication involves low power and is effective at short ranges, e.g. close to a wireless network transceiver 60 or network server (40 and 42). Portable radiotelephone communication, on the other hand, utilizes more power and operates at greater ranges. To initiate a wireless communication link with the ICS network 10, the local ICS module 304 determines whether the communications profile for the desired network server (40 or 42) is stored on-board the point of care terminal (20 or 22). If it is, the ICS module 304 attempts to initiate a communication link with the network server (40 or 42) via the cordless telephone transceiver 310. If a communication link cannot be established, the local ICS module then attempts to initiate a communication link via the portable radiotelephone transceiver 308. If a communication link again cannot be established, the local ICS module 304 sends a message to the user via the video display 306, to connect the point of care terminal (20 or 22) to an RS232 connector via the modem/PCMCIA interface 312. Once the unit is connected to a PSTN 45, the ICS module 304 places a telephone call to a network server (40 and 42) and initiates communication with the ICS network 10. If the user does not connect the unit to a PSTN 45 via the modem/PCMCIA interface 312 after a predetermined period of time, or if the user indicates through input device 316 that a wired connection is not desired, the local ICS module 304 configures the point of care terminal to operate in local capture mode such that all data entered by the user is stored in secondary storage 318 until it can be uploaded to the ICS network 10.

If the communications profile for the desired network server is not stored on-board the point of care terminal (20 or 22), the ICS module 304 initiates communication with the ICC database server 50 utilizing the same scheme previously discussed (i.e., local wireless Ethernet, then remote wireless Ethernet, and then PSTN). Once communication with the ICC is established, the ICS module retrieves the communication profiles from the ICC database server 50 and then initiates communication with the desired network server (40 or 42), utilizing the same method previously discussed.

The CPU 314 is preferably an IBM™ compatible computer based on an Intel™ Pentium™ processor. Operating in memory 302 is a client software module 303 compatible with the software in the ICS module 304. The client software module 303 is a user-friendly software interface that authenticates users desiring who desire access to point of care terminals, and allows users of the point of care terminal (20 and 22) to input data into a patient record and/or modify data already found in an existing record using simple key strokes. An assortment of blank medical forms typically required by medical professionals are also stored in memory 302 and may be accessed via the client software module 303.

The input device 316 accepts data entry caused by a stylus impacting the electronic video display integral to each point of care terminal. Software operating on the point of care terminal 20 provides a graphical interface through which digital forms and other information may be retrieved by the user for manipulation and subsequent upload to the ICC 50. For specialized applications, the point of care terminal 20 can also be configured to accept keyboard, bar-code reader, or other inputs. Secondary storage 318 will be used by the point of care terminal to store digitally stored forms and patient data when the terminal is not capable of accessing the ICS network either through a wired or wireless interface. Finally, antenna 320 is used to transmit data when the point of care terminal is either in a cellular transmission or local wireless LAN communication mode.

Figure 3:
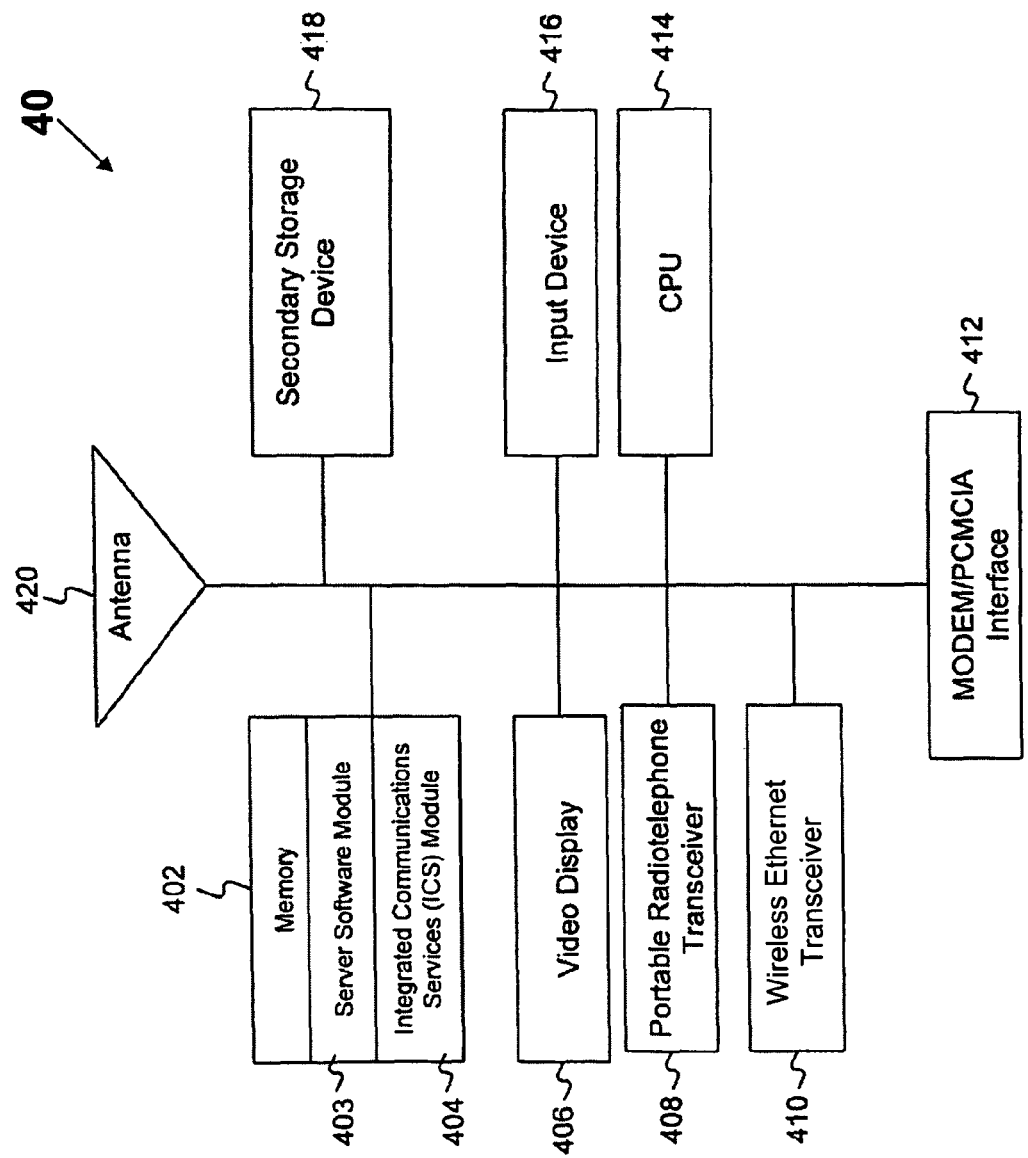
FIG. 3 is a more detailed block diagram of the network server of FIG. 1.

FIG. 3 shows a detailed block diagram of a network server (40 or 42). Like point of care terminals (20 and 22), network servers (40 and 42) are comprised of a memory 402, a server software module 403, a local ICS module 404, video display 406, a portable radiotelephone transceiver 408, a wireless Ethernet transceiver 410, a Modem/PCMCIA interface 412, a central processing unit (CPU) 414, an input device 416, a secondary storage 418 and an antenna 420.

Operating in memory 402 is the server software module 403 and the local ICS module 404. The server software module 403 simultaneously supports local users inside of the hospital 30 and remote users accessing the ICS network 10 via a wireless or wireline interface. For local users, the server software module 403 is similar to the client software module 303 that operates on the point of care terminals (20 and 22). It authenticates users and allows them to input data into a patient record or modify data already found in an existing record using simple key strokes. Local ICS module 404 is similar to the ICS module 304 operating on the point of care terminal in that it provides the network server with the capability to communicate with other network servers (40 and 42) and the ICC database server 50 using several attached communication channels. In a preferred embodiment, the local ICS module 404 will be larger than the ICS module 304, and may even be large enough to store the communication profiles for all network servers (40 or 42) resident on the ICS network 10. Memory 402 also is comprised of an assortment of blank medical forms typically required by medical professionals in the course of diagnosing and treating patients.

For remote users accessing the ICS network via the network server (40 or 42), the server software module 403 displays at least a first "home page" that permits remote users to log onto the network 10 and access patient, testing and payment information. In the preferred embodiment, the server software module 403 supports simultaneous wireless access to the network by numerous users, as well as simultaneous access across different communications protocols. As shown in FIG. 1, network server 42 located in the emergency room 35, is capable of simultaneously communicating with a plurality of point of care terminals in dispatched ambulances. While not shown, the network server (40 and 42) can also simultaneously support a plurality of remote wireless and local wireless users with a wireline user. As is known in the art, this contact can be established on a network such as the Internet by sending data packets to an electronic address associated with the host system.

Figure 4:
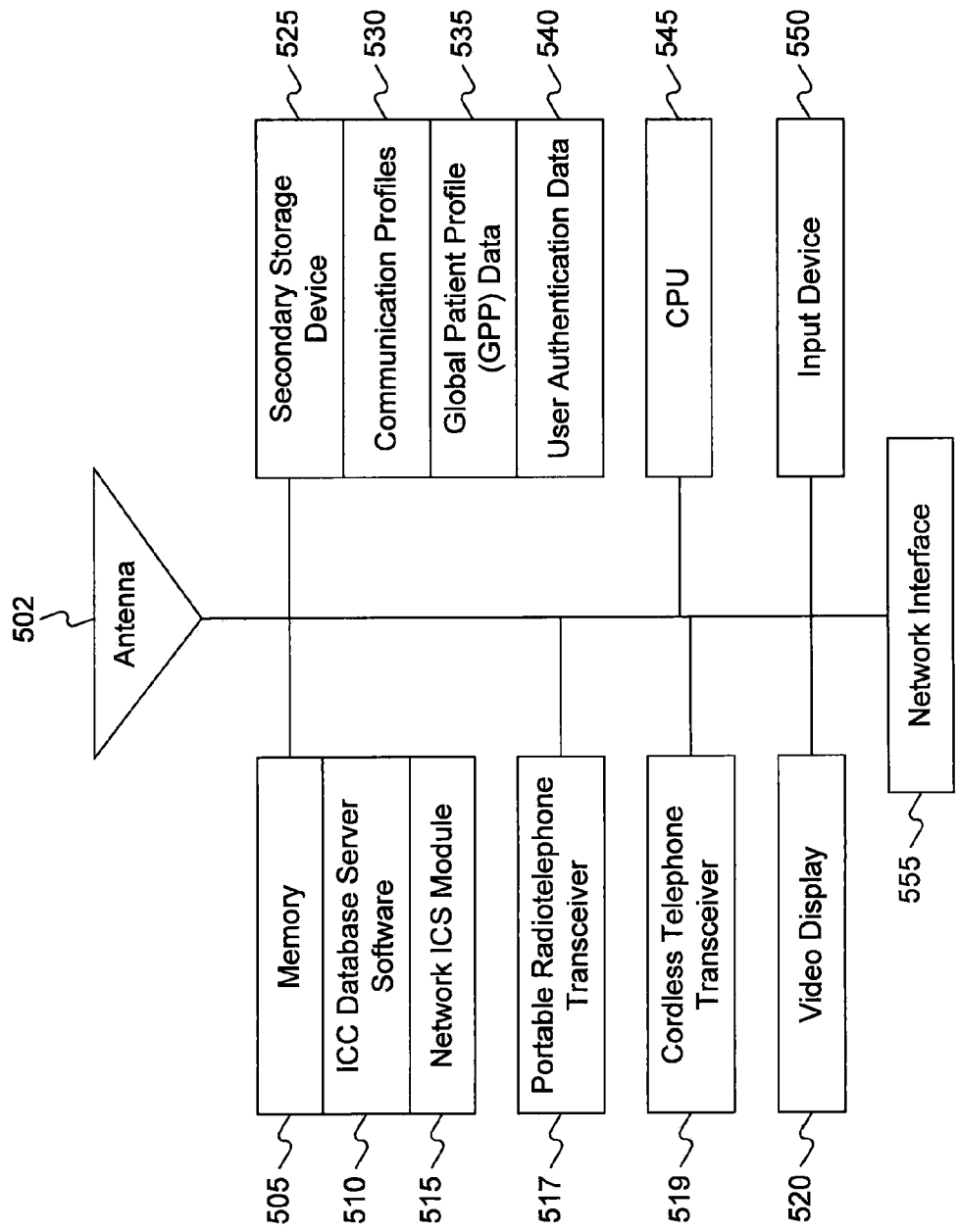
FIG. 4 a more detailed block diagram of the ICC server of FIG. 1.

FIG. 4 shows a detailed block diagram of an ICC database server 50. As shown in FIG. 4, an ICC database server 50 includes an antenna 502, memory 505, ICC database server software 510, a network ICS module 515, a portable radiotelephone transceiver 517, a cordless telephone transceiver 519, a video display 520, a secondary storage device 525, communication profiles 530, global patient profile (GPP) data 535, user authentication data 540, CPU 545, an input device 550, and a network interface 555.

Antenna 502, portable radiotelephone transceiver 517, cordless telephone transceiver 519, video display 520, input device 550, and network interface 555 are similar to the identically-named components installed in network servers (40 and 42) and point of care terminals (20 and 22). For the sake of brevity, their functions will not be described again.

Operating in memory 505 of the ICC database server 50 is the ICC database server software 510 and the network ICS module 515. After receiving a request to access the ICC database server 50, ICC database server software 510 authenticates users, searches the secondary storage device for patient data, adds new patient data and deletes patient data, when requested. The ICC database server software 510 also has the ability to provide aggregated GPP data and demographic information (with or without patient identification), creating "live" public health statistics through a single query to a central server. The ICC database server software 510 further includes a data management, storage, and retrieval application that organizes the information exchanged between hospitals, laboratories, dispatched ambulances and insurance carriers. This information is organized and stored within the ICC database server 50 on one or more ICC secondary storage devices 525. The software architecture underlying the particular preferred embodiment is also based upon the hypertext conventions of the World Wide Web. A more detailed explanation of the operation of the ICC database server software 510 is provided with reference to FIG. 9.

The network ICS module 515 performs the functions necessary to provide network access (wireless or wireline) to point of care terminals (20 or 22) and network servers (40 and 42). When it receives a request for network access, the network ICS module will either perform the processing necessary to provide network access or it will pass the requested information back to a point of care terminal (20 or 22) for processing by a local ICS module 304. A more detailed explanation of the operation of the network ICS module 515 is provided with reference to FIG. 7.

Secondary storage device 525 is used to store the communication profiles 530, global patient profile (GPP) data 535, and the user authentication data 540. The communication profiles 530 are the detailed communication parameters necessary for communicating with each server operating on the ICS network 10. These communication profiles 530 are downloaded from the ICC database server 50 to requesting point of care terminals (20 and 22) and network servers (40 and 42) that wish to communicate with a specific network resource. Global patient profile (GPP) data 535 is the type of data typically found in a patient's medical records. GPP data includes historical treatment data, patient allergies, physical characteristics, etc. Each time a new patient is added to the system, it constructs a patient profile, that is then passed to the ICC database server 50 for archival purposes. As a result, whenever the need arises to examine patient data, the file can be downloaded from the ICC to the patient care provider for evaluation.

Figure 5:
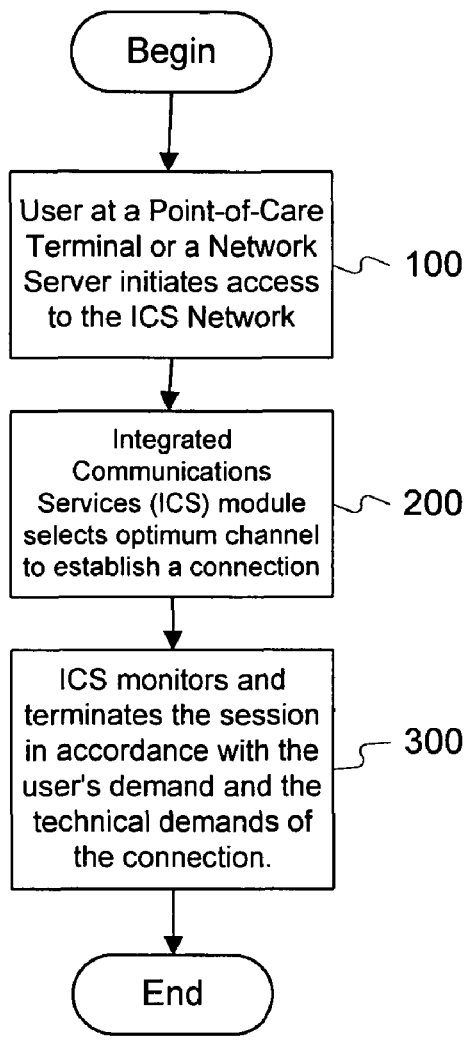
FIG. 5 is a flow chart showing the operation of the integrated communications services network in a manner consistent with the present invention.
Figure 6:
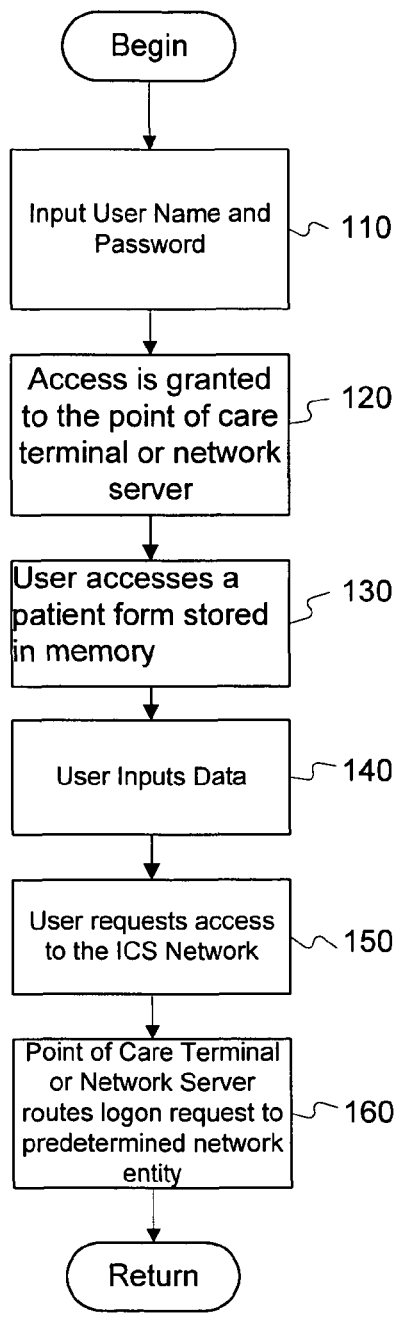
FIG. 6 is a flow chart of the process for initiating access to the integrated communications services network.

The process of accessing the ICS network 10 begins when a user at a point of care terminal (20 or 22) or a network server (40 or 42) initiates access to the point of care terminal or network server. FIG. 5 is a flowchart of the access operation for a user at a point of care terminal (20 and 22) or network server (40 or 42). A user initiates access to the ICS network in step 100. Next in step 200, the ICS module (local or remote) selects an optimum channel to establish a communication link. Once the user gains access to the network, the ICS module (local or remote) monitors the access session and then terminates the session in accordance with the user's demand and the technical demands of the connection (step 300). Referring now to FIG. 6, the steps performed when a user at a point of care terminal or network server initiates access to the ICS network as shown in step 100 (FIG. 4) will be explained in greater detail. First as depicted in step 110, the user enters his/her password in step to gain access to point of care terminal or network server. Passwords will be assigned to correspond with the user's position in the medical hierarchy. For example, all physician's will have similar passwords and all insurance claims agents will have similar passwords. When the user gains access to the network data in step 120, he/she will only be permitted to execute the functions normally performed by other individuals of the user's occupation. For example, a nurse or an EMT will only be permitted to execute the tasks normally performed by other nurses and EMTs. Simply stated, a logged on nurse will not be permitted to report or change the results of a laboratory test. A lab technician correspondingly, will not be permitted to order a test for a patient. After the user gains access to the point of care terminal or network server in step 120, he/she may then access a plurality of forms stored on the point of care terminal (20 and 22) or the network server (40 or 42) in step 130. The specific forms accessed will be dependent on the user's desired objective. It is intended that all forms resident on the point of care terminal (20 or 22) will simply require a series of simple stylus depressions on a touch screen to complete. For example, it is expected that most textual information will be selectable through a multiple choice user interface, so as to record detailed treatment and diagnostic information in very little time. Forms resident on the network server (40 or 42), on the other hand, will be completed using conventional input means (keyboard, mouse, etc.) In step 140, the user inputs data onto the retrieved form. When the user on a point of care terminal (20 or 22) or network server (40 or 42) completes inputting information that either seeks to retrieve information or to supplement data stored on a network server, he/she requests access to the ICS network in step 150. Once the user transmits his/her request, processing flows to step 160 where the point of care terminal (20 or 22) or the network server (40 or 42) routes the request to a predetermined network entity (network server, or wireless transceiver, respectively). Each network server (40 or 42) and wireless transceiver has its own unique access dial-up number. When a point of care terminal (20 or 22) or network server (40 or 42) is initially set-up, a predetermined dial-up number is stored in the computer's memory such that unless manually overridden by the user, all attempts to access the ICS network 10 through the point of care terminal (20 or 22) or network server (40 or 42) will automatically be routed to the same network entity (network server or wireless transceiver). Managing wireless traffic in this way prevents processing bottlenecks that plague many other prior art wireless networks because it reduces the likelihood that an inordinate amount of users will attempt to log onto the same or a very few number of network server locations. After the request for ICS network 10 access has been routed to the predetermined network entity, program execution returns to step 200 of (FIG. 5).

Figure 7A:
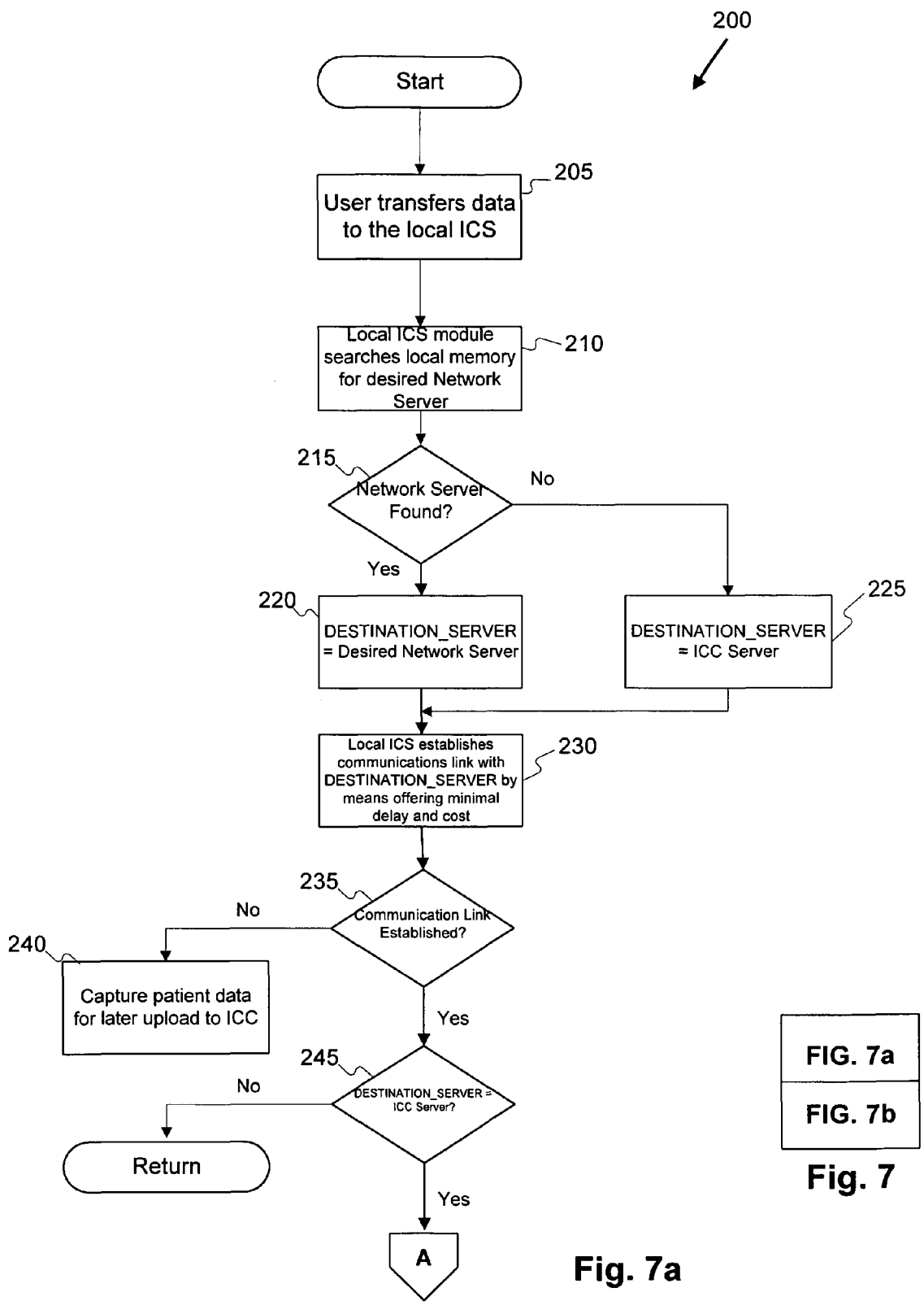
FIG. 7 is a flow diagram of the process for selecting the optimum channel to establish a connection to the ICS network.
Figure 7B:
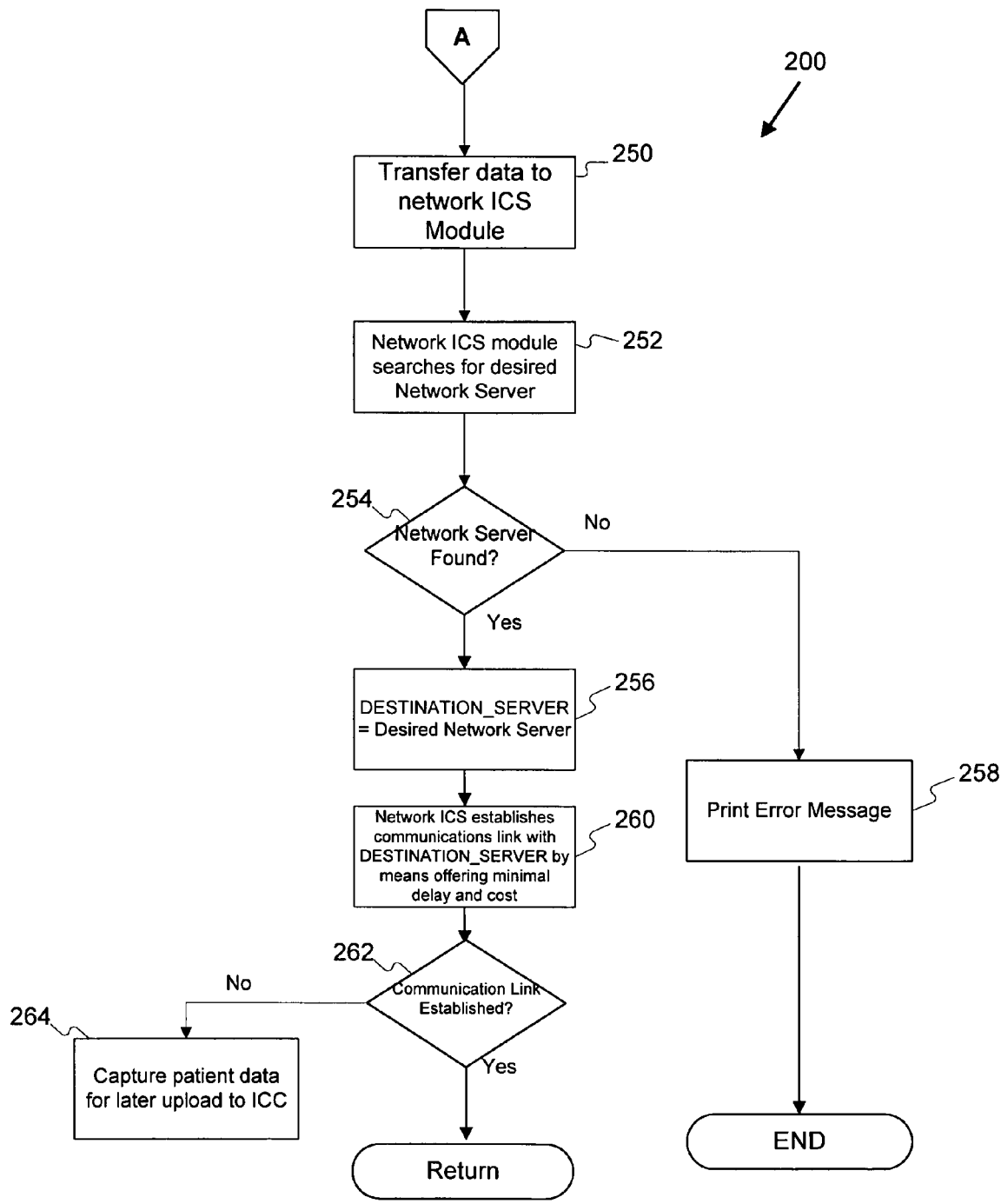

FIG. 7 is a flow diagram illustrating the method depicted in step 200 (FIG. 5) in which the local ICS module determines whether it can process a user's request for access to the ICS network 10 or whether it must pass the logon request to the network ICS module 515 operating on the ICC server 50. As previously mentioned, the specific ICS module (local or network) that processes a logon session is dependant on whether the desired network server destination (and therefore its communication profile) is stored in the local ICS module (resident in the point of care terminal (20 or 22) or in the network server (40 or 42)). If it is, processing will be controlled by the local ICS module. If, on the other hand, the desired network destination cannot be found in the local ICS module, network access will be facilitated through the network ICS module. As shown in step 205, the process begins when a user transfers data to the local ICS module. The data is comprised of a desired network destination together with newly modified patient data. Upon receipt of the transferred data, the local ICS module in step 210 searches local memory for the desired network server. As mentioned earlier, the desired network server can either be the pre-programmed network entity, or it can be a user-inputted network entity. If the local ICS module finds a communication profile that corresponds to the desired network server in step 215, the local ICS module assigns the desired network server ID to the DESTINATION_SERVER variable in step 220 and then it establishes a communication link with the designated destination server by means offering the shortest delay and minimal cost (step 230). Program execution then flows to step 235. If the local ICS module does not find a communication profile that corresponds to the desired network server in step 215, processing flows to step 225 where the ICS module assigns the ICC database server ID to the DESTINATION_SERVER variable. The local ICS module then establishes a communication link with the ICC database server 50 for the purpose of locating the communication profile on the ICC database server 50 in step 230. Program execution then flows to step 235 where the local ICS module determines whether a communication link has been established. If a communication link has not been established, execution flows to step 240 and the point of care terminal (20 or 22) or the network server (40 or 42) is configured to locally capture data until connectivity with the ICS network 10 can be established. In other words, if the point of care terminal or network server cannot be connected to the desired network server or ICC database server, the terminal or server is placed into local capture mode. If a communication link is established in step 235, the local ICS server then determines whether the DESTINATION_SERVER variable is set to the ICC server (step 245). If the DESTINATION_SERVER variable is not equal to the ICC server 50, a successful link with a desired network server has been established and processing execution returns to step 300 (FIG. 5). On the other hand, if the DESTINATION_SERVER variable is set to the ICC server, program execution flows to step 250 and the local ICS module transfers data to the network ICS module operating on the ICC database server 50. As shown in FIG. 7*b*, processing next flows to step 252 and the network ICS module searches the secondary storage device 525 for the desired network server and its corresponding communication profile 530. If the network server is found in step 254, processing flows to step 256 and the remote ICS module assigns the desired network server ID to the DESTINATION_SERVER variable. The remote ICS module then establishes a communication link with the designated destination server by means offering the shortest delay and minimal cost (step 260). Program execution then flows to step 262 where the remote ICS module determines whether a communication link has been established. If a communication link has not been established, execution flows to step 264 and the remote ICS module instructs the local ICS module to configure the point of care terminal (20 or 22) or the network server (40 or 42) to locally capture data. If the remote ICS module does not find a communication profile corresponding to the desired network server in step 254, processing flows to step 258 where an error message is transmitted to the user informing him that the desired network server is not present on the ICS network 10, and processing terminates.

Figure 8:
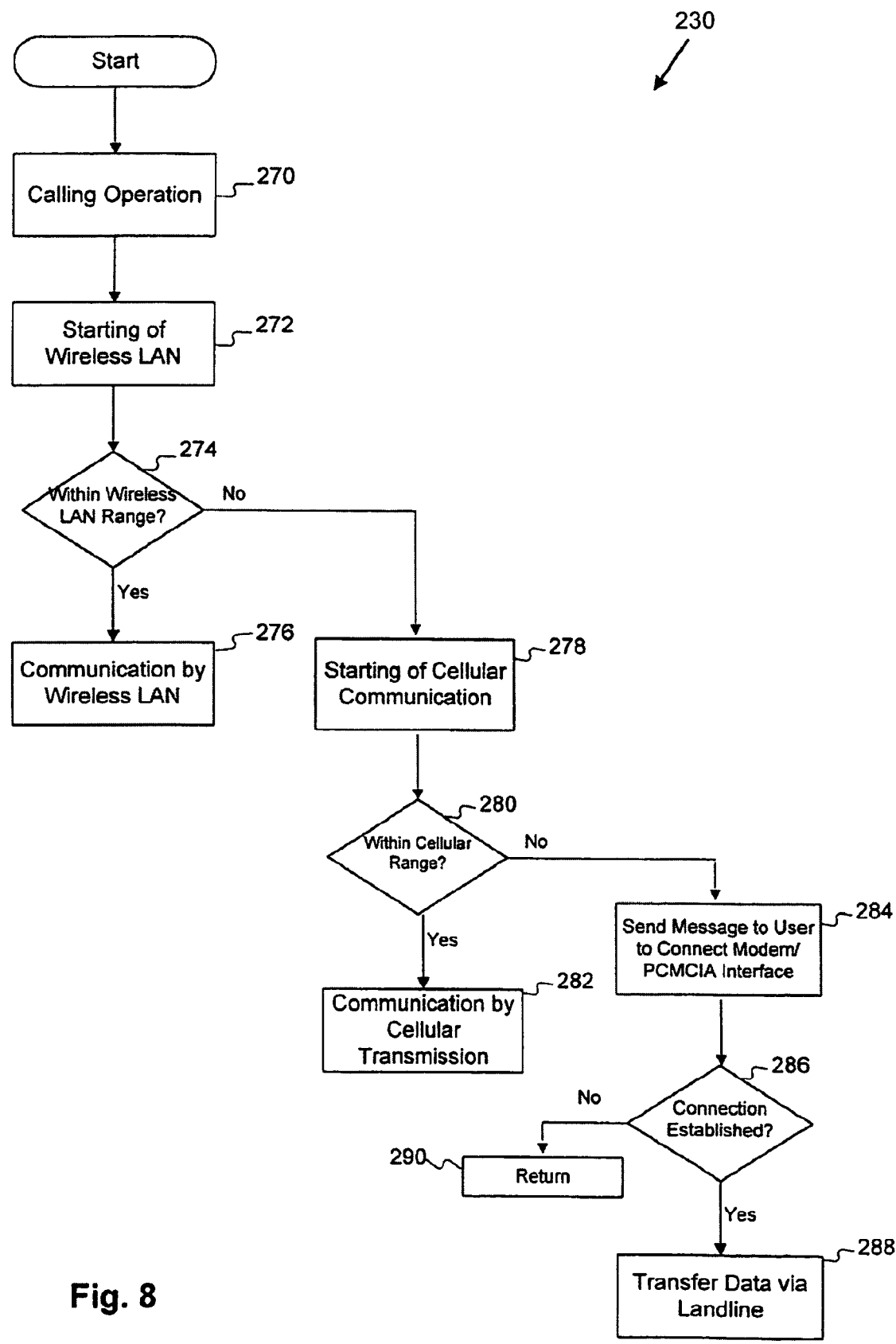
FIG. 8 is a flow diagram of the process for scanning the available communication channels.

FIG. 8 depicts the processing performed by the ICS module (local or remote) to establish communications as described in step 230 of FIG. 7*a* (or step 260 of FIG. 7*b*). As shown in step 270, after the ICS module has determined that a communication link is available to the desired target, it terminates its inquiry operations and begins a calling operation. This process is best illustrated by way of example. Table 1 is an example of the communication profiles that may be stored in either the local ICS module (304 or 404) or the network ICS module 515. In addition to the information shown in Table 1, the systems may additional store information like IP address, TCP timers and their values, type of protocol, data compression format, and forward error correction toggle.

TABLE 1

| Network Server | Wireless Ethernet | Wired Ethernet | 56 Kb wired modem | Cellular Data |
|---|---|---|---|---|
| A | ✓ | ✓ | | ✓ |
| B | | ✓ | | |
| C | | | ✓ | |
| D | ✓ | | | |
| E | | | | ✓ |

Imagine that a user at a point of care terminal 20 would like to communicate with network server A. Referring to Table 1, it is seen that network server A can either communicate via wireless ethernet, wired ethernet or the cellular network. The local ICS module 304 first attempts to communicate via the wireless LAN (step 272). Toward that end, the ICS module 304 determines whether the point of care terminal or network server is in range of the wireless LAN in step 274. If the ICS module 304 determines that the wireless LAN is in range, a communication link is established via the wireless LAN. If, in step 274, the ICS module 304 determines that the wireless LAN is out of range, it attempts to communicate via the cellular communication network in step 278. If the remote computer is within a cellular network (step 280), the system establishes a communication link via the cellular communication network in (step 282). If the remote computer is outside of a cellular network, which could be the case in remote areas, a message is transmitted to the screen that instructs the user to connect the internal modem/PCMCIA interface to an appropriate RS232 telephone jack (step 284). This is necessary to establish connectivity to the PSTN 45. If the connection is established in step 286, a data link is established via a landline and data is transferred via the landline (step 288). Otherwise, processing returns to step 205 or step 250 via step 290 (depending on whether the calling program was the local ICS module or the network ICS module.) If instead of wishing to communicate with network server A, the point of care terminal (20 or 22) desires to communicate with network server B, the local ICS would attempt to first communicate via a wireless LAN interface. This gives the user at a point of care terminal (20 or 22) more flexibility than a wired connection and it could be accomplished at a very minimal cost compared to cellular or PSTN (depending upon the distance to be traveled and the amount of time for the data communication). Finally, suppose that the point of care terminal (20 or 22) chose instead to communicate with network server C. In that case, communication across wireless ethernet would not be appropriate because network server C only has access via a 56 Kb wired modem. To effect the communication link, the local ICS module 304 would first attempt to establish a cellular link. If that was not successful or not possible given the point of care terminal's (20 or 22) location, the local ICS module 304 would then instruct the user to connect the point of care terminal (20 or 22) to the PSTN 45 for a wired transmission link. Only if that failed would the ICS module 304 initiate local data capture.

Figure 9:
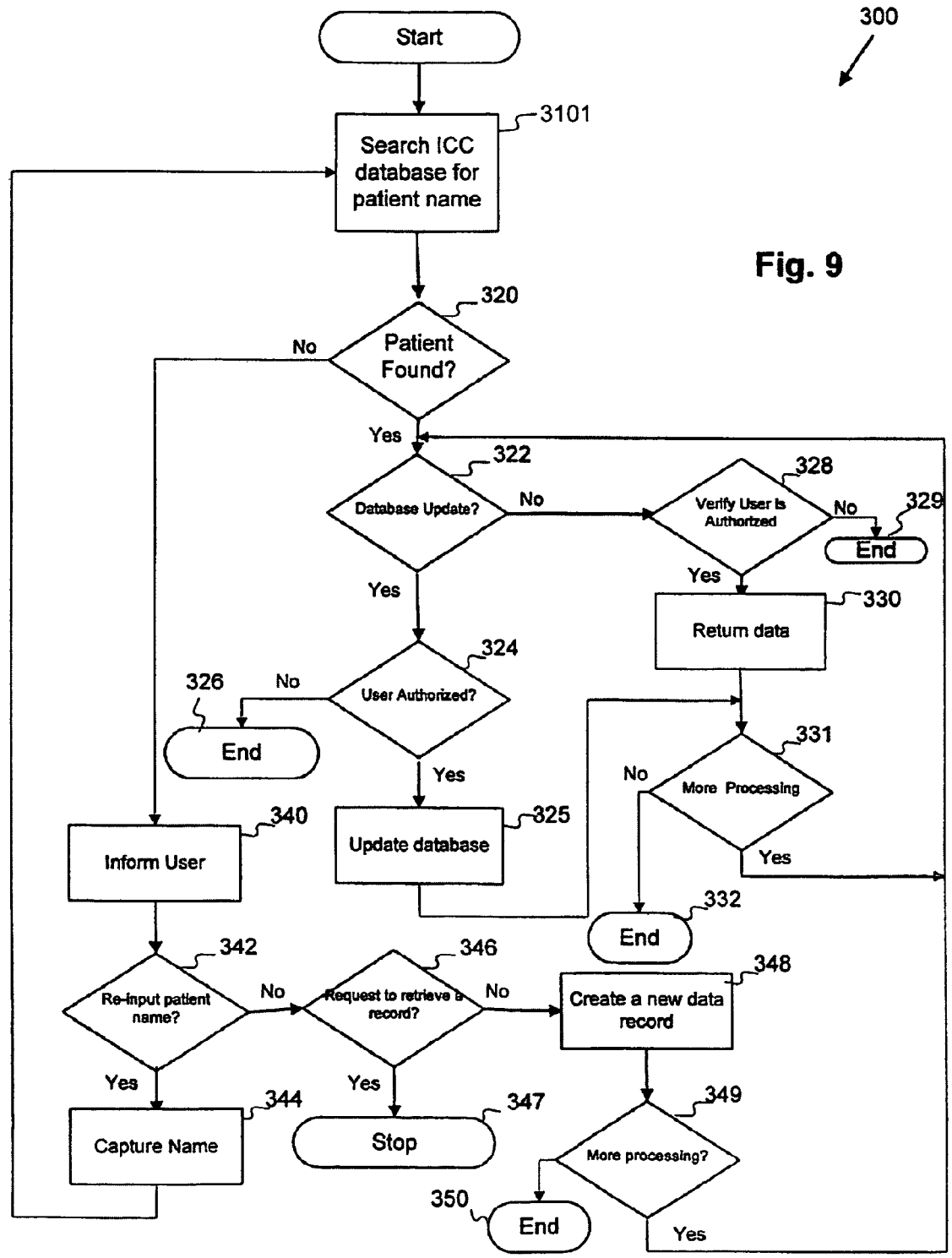
FIG. 9 is a flow diagram of the process of monitoring a connection session of FIG. 5.

FIG. 9 depicts the processing performed by step 300 (FIG. 5) as the ICS module monitors and eventually terminates the session. First, in step 3101, ICC database server software 510 searches the ICC database server 50 for the inputted patient name. If the patient name is found in step 320, the ICC database server software 510 then determines in step 322 whether the user data is a database update. If the user seeks to update the GPP data 535 (or one of the associated network servers), the ICC database server software 510 verifies that the user is authorized to update the data (step 324) and if the user is authorized, the database is updated in step 325 and processing flows to step 331. In step 331, the ICS module determines from the user's action whether there is more processing to be performed. If there is, program execution branches to step 322, otherwise processing terminates in step 332. If the user is not authorized to update the database in step 324, he/she is informed that they do not have required authorization and processing terminates in step 326. If, in step 322, the ICC database server software 510 determines that the user is instead attempting to access database information (in other words the user is not attempting to update the database), it verifies whether the user is authorized to access the data in step 328 and then returns the data to the authorized user in step 330. Processing then flows to step 331 and the ICS module determines whether there is any more processing to be performed. If the user in step 328 is not authorized to access the data, processing terminates in step 329.

If the ICC database server does not find the patient name in step 320, a message is transmitted back to the user on the remote computer informing them that the patient was not found (step 340), and the user is given another opportunity to re-input the patient's name in step 342. If the user re-inputs a new patient name in step 344, processing flows to step 3101, and the ICC database server software 510 again searches the ICC database server for the inputted patient's name. If the user does not re-input a new patient name, processing flows to step 346 and the ICC database server software 510 determines whether the user is attempting to access a database record. If the user is attempting to access a non-existent database record (and does not re-input a new patient name) processing terminates in step 347. Otherwise a new record is created in the ICC database server for the new patient (step 348) and a message is transmitted back to the remote computer informing the user that a new record was created. Also, as stated earlier a Global Patient Profile (GPP) record is sent to the ICC when processing terminates. The diversity and coverage of the information contained in the GPP database will assist medical services planners in assessing the utility and effectiveness of all observed medical phenomenon without revealing a patient's identity. The ICS module ascertains whether the user would like to perform more processing in step 349. If he/she does, processing returns to step 322, otherwise the program execution terminates in step 350.

From the foregoing description, it will be appreciated that the present invention provides an efficient system and method for reading package information. The present invention has been described in relation to particular embodiments which are intended in all respects to be illustrative rather than restrictive. Those skilled in the art will appreciate that many different combinations of hardware will be suitable for practicing the present invention. Many commercially available substitutes, each having somewhat different cost and performance characteristics, exist for each of the components described above.

Although aspects of the present invention are described as being stored in memory, one skilled in the art will appreciate that these aspects can also be stored on or read from other types of computer-readable media, such as secondary storage devices, like hard disks, floppy disks, or CD-ROMs; a carrier wave from the Internet; or other forms of RAM or ROM. Similarly, the method of the present invention may conveniently be implemented in program modules that are based upon the flow charts in FIGS. 5-9. No particular programming language has been indicated for carrying out the various procedures described above because it is considered that the operations, steps and procedures described above and illustrated in the accompanying drawings are sufficiently disclosed to permit one of ordinary skill in the art to practice the instant invention. Moreover, there are many computers and operating systems which may be used in practicing the instant invention and therefore no detailed computer program could be provided which would be applicable to these many different systems. Each user of a particular computer will be aware of the language and tools which are most useful for that user's needs and purposes.

Alternative embodiments will become apparent to those skilled in the art to which the present invention pertains without departing from its spirit and scope. Accordingly, the scope of the present invention is defined by the appended claims rather than the foregoing description.

What is claimed is:

1. A method of accessing an information system using a portable access device, the method comprising:
   receiving a request from said portable access device to access a network server;
   identifying a communication profile associated with said network server, the communication profile including description information corresponding to a data compression format and a forward error correction toggle;
   transmitting said communication profile to said portable access device;
   establishing a communication link between said portable access device and said network server using a communication channel that is selected based on said communication profile, a location of said portable access device with respect to said network server, a desired quality of the communication link, and a cost of the communication link, the communication link being established by using the selected communication channel when no user action is required to establish the communication link, wherein said communication channel is selected from the group consisting of: local wireless LAN, remote wireless LAN, wireline LAN, and Public Switched Telephone Network (PSTN), and establishing the communication link includes using at least a portion of the description information; and
   displaying a notification to instruct a user to perform a user action to establish the communication link when the user action is required to establish the communication link.

2. The method of claim 1 further comprising the step of configuring said portable access device to capture data in memory in accordance with a failed attempt to establish said communication link.

3. The method of claim 1 wherein said step of identifying a communication profile associated with said network device further comprises the following steps:
   accessing a central database;
   searching said central database for a communication profile associated with said network server; and
   retrieving said communication profile.

4. The method of claim 1 wherein said step of establishing communication between said portable access device and said network server is further comprised of the following steps:
   configuring said portable access device to transmit using one of a plurality of communication channels in accordance with said communication profile;
   verifying the availability of said communication channel; and
   initiating communication between said portable access device and said network server using one of said communication channels.

5. The method of claim 1 wherein establishing a communication link comprises:
   transmitting a first request to a local wireless LAN transceiver;
   transmitting a second request to a remote wireless transceiver when a communication link cannot be established with said local wireless LAN transceiver; and
   connecting to a PSTN when a communication link cannot be established with said remote wireless transceiver.

6. A method of accessing an information system using a portable access device, the method comprising:
   identifying a communication profile associated with a first network server, the communication profile including description information corresponding to a data compression format and a forward error correction toggle;

attempting, by the portable access device, to establish a communication link between the portable access device and the first network server using communication channel that is selected by the portable access device based on the communication profile, a location of the portable access device with respect to the first network server, a desired quality of the communication link, and a cost of the communication link, wherein the communication channel is selected from the group consisting of: a local wireless LAN, a remote wireless LAN, a wireline LAN, and a Public Switched Telephone Network (PSTN), and attempting to establish the communication link includes using at least a portion of the description information;

capturing data received by the portable access device in a memory located in the portable access device in accordance with a failed attempt to establish the communication link;

establishing the communication link by using the selected communication channel when no user action is required to establish the communication link; and displaying a notification to instruct a user to perform a user action to establish the communication link when the user action is required to establish the communication link.

7. The method of claim 6 wherein said step of identifying a communication profile associated with said network server further comprises the following steps:

searching an internal database for a communication profile associated with the first network server; and retrieving said communication profile from the internal database.

8. The method of claim 6 wherein said step of attempting to establish a communication link with said first network server is further comprised of the following steps:

configuring said portable access device to transmit using one of a plurality of communication channels, in accordance with said communication profile;

verifying the availability of said communication channel; and initiating communication between said portable access device and said network server along said communication channel.

9. The method of claim 6 wherein attempting to establish a communication link server comprises:

transmitting a first request from said portable access device to a local wireless LAN transceiver;

transmitting a second request from said portable access device to a remote wireless transceiver when a communication link cannot be established with said local wireless LAN transceiver; and requesting a connection to a PSTN when a communication link cannot be established with said remote wireless transceiver.

10. The method of claim 6 wherein the identifying comprises:

searching an internal database of the portable access device for the communication profile associated with the first network server;

transmitting from the portable access device to a second network server, a request to access the first network server when the communication profile cannot be found in the internal database; and retrieving the communication profile server from the second network server.

11. The method of claim 10 wherein transmitting a request from the portable access device to the second network server comprises:

transmitting a first request from the portable access device to a local wireless LAN transceiver;

transmitting a second request from the portable access device to a remote wireless transceiver when a communication link cannot be established with the local wireless LAN transceiver; and connecting the portable access device to a public switched telephone network (PSTN) when a communication link cannot be established with the remote wireless transceiver.

12. A method of access an information system using a portable access device, the method comprising:

transmitting from said portable access device to a first network server, a request to access a second network server;

receiving said request at said first network server;

identifying a communication profile associated with said second network server, the communication profile including description information corresponding to a data compression format and a forward error correction toggle;

transmitting said communication profile from said first network server to said portable access device;

establishing a communication link between said portable access device and said second network server using a communication channel that is selected based on said communication profile, a location of said portable access device with respect to said second network server, a desired quality of the communication link, and a cost of the communication link, the communication link being established by using the selected communication channel when no user action is required to establish the communication link, wherein said communication channel is selected from the group consisting of: local wireless LAN, remote wireless LAN, wireline LAN, and Public Switched Telephone Network (PSTN), and establishing the communication link includes using at least a portion of the description information;

displaying a notification to instruct a user to perform a user action to establish the communication link when the user action is required to establish the communication link.

13. The method of claim 12 further comprising the step of configuring said portable access device to capture data in memory in accordance with a failed attempt to establish said communication link.

14. The method of claim 12 wherein said step of transmitting from a portable access device to a first network server is further comprised of the following steps:

transmitting a first request from a portable access device to a local wireless LAN transceiver;

transmitting a second request from said portable access device to a remote wireless transceiver when a communication link cannot be established with said local wireless LAN transceiver; and connecting said portable access device to a public switched telephone network (PSTN) when a communication link cannot be established with said remote wireless transceiver.

15. The method of claim 12 wherein identifying a communication profile further comprises:

accessing a central database; and retrieving a communication profile that corresponds to said second network server.

16. The method of claim 12 wherein establishing a communication link comprises:
configuring said portable access device to transmit using one of a plurality of communication channels in accordance with said communication profile;
verifying the availability of a communication channel; and
initiating communication between said portable access device and said second network server along said communication channel.

17. The method of claim 12 wherein establishing a communication link comprises:
transmitting a first request to a local wireless LAN transceiver;
transmitting a second request to a remote wireless transceiver when a communication link cannot be established with said local wireless LAN transceiver; and
connecting to a PSTN when a communication link cannot be established with said remote wireless transceiver.

18. A method of accessing an information system using a portable access device, the method comprising:
identifying, by the portable access device, a communication profile associated with a first network server, wherein the identifying a comprises:
searching an internal database for the communication profile;
transmitting from the portable access device to a second network server, a request to access the first network server when the communication profile cannot be found in the internal database; and
retrieving the communication profile from the second network server, the communication profile including description information corresponding to a data compression format and a forward error correction toggle;
attempting, by the portable access device, to establish a communication link between the portable access device and the first network server using one of a plurality of communication media, in accordance with the communication profile, a desired quality of the communication link, and a cost of the communication link, wherein the one of a plurality of communication media is selected from the group consisting of: a local wireless LAN, a remote wireless LAN, a wireline LAN, and a Public Switched Telephone Network (PSTN), and attempting to establish the communication link includes using at least a portion of the description information;
capturing data in a memory location in accordance with a failed attempt to establish the communication link;
establishing the communication link by using the selected communication media when no user action is required to establish the communication link; and
displaying a notification to instruct a user to perform a user action to establish the communication link when the user action is required to establish the communication link.

19. The method of claim 18 wherein transmitting a request from the portable access device to the second network server comprises:
transmitting a first request from the portable access device to a local wireless LAN transceiver;
transmitting a second request from the portable access device to a remote wireless transceiver when a communication link cannot be established with the local wireless LAN transceiver; and
connecting the portable access device to a public switched telephone network (PSTN) when a communication link cannot be established with the remote wireless transceiver.

20. A method of accessing information using an access device, the method comprising:
identifying, by the access device, a communication profile associated with a first server, the communication profile including description information corresponding to a data compression format and a forward error correction toggle;
attempting, by the access device, to establish a communication link between the access device and the first server, in accordance with the communication profile, a desired quality of the communication link, and a cost of the communication link, wherein the attempting includes initiating a first attempt to establish communication with the first server via a local wireless network, initiating a second attempt to establish communication via a remote wireless network if the first attempt fails, and initiating a third attempt to establish communication via a public switched telephone network if the second attempt fails;
establishing the communication link when no user action is required to establish the communication link, wherein establishing the communication link includes using at least a portion of the description information;
displaying a notification to instruct a user to perform a user action to establish the communication link when the user action is required to establish the communication link; and
accessing the information from the first server when the communication link is established.

21. The method of claim 20, wherein identifying a communication profile comprises:
determining, by the access device, whether or not the communication profile is stored locally by the access device; and
establishing communication with a second server to retrieve the communication profile, if the communication profile is not stored locally.

22. The method of claim 21, wherein establishing communication with the second server comprises:
initiating a first attempt to establish communication via a local wireless network, initiating a second attempt to establish communication via a remote wireless network if the first attempt fails, and initiating a third attempt to establish communication via a public switched telephone network if the second attempt fails.

23. The method of claim 20, further comprising:
configuring the access device to operate in a local capture mode such that data received by the access device is stored in a memory located in the access device, if the third attempt fails.

24. A computer-readable storage device containing instructions which, when executed by a processor, perform a method for accessing an information system comprising an access device and a plurality of network servers, the method comprising:
receiving a request from a portable access device to access a network server;
identifying a communication profile associated with said network server, the communication profile including description information corresponding to a data compression format and a forward error correction toggle;
transmitting said communication profile to said portable access device;
establishing a communication link between said portable access device and said network server using one of a plurality of communication channels that is selected based on said communication profile, a location of said portable access device with respect to said network server, a desired quality of the communication link, and a cost of the communication link, the communication link being established by using the selected communication channel when no user action is required to establish the communication link, wherein said communication channel is selected from the group consisting of: local wireless LAN, remote wireless LAN, wireline LAN, and Public Switched Telephone Network (PSTN), and establishing the communication link includes using at least a portion of the description information; and displaying a notification to instruct a user to perform a user action to establish the communication link when the user action is required to establish the communication link.

25. The computer-readable storage device of claim 24 further comprising the step of configuring said portable access device to capture data in memory in accordance with a failed attempt to establish said communication link.

26. The computer-readable storage device of claim 24 wherein said step of identifying a communication profile associated with said network device further comprises the following steps:
accessing a central database;
searching said central database for a communication profile associated with said network server; and
retrieving said communication profile.

27. The computer-readable storage device of claim 24 wherein said step of establishing communication between said portable access device and said network server further comprises of the following steps:
configuring said portable access device to transmit using one of a plurality of communication channels in accordance with said communication profile;
verifying the availability of said communication channel; and
initiating communication between said portable access device and said network server using one of said communication channels.

28. The computer-readable storage device of claim 24 wherein establishing communication comprises:
transmitting a first request to a local wireless LAN transceiver;
transmitting a second request to a remote wireless transceiver when a communication link cannot be established with said local wireless LAN transceiver; and
connecting to a PSTN when a communication link cannot be established with said remote wireless transceiver.

29. A computer-readable storage device containing instructions which, when executed by a processor, perform a method for accessing an information system comprising a portable access device and a plurality of network servers, the method comprising:
identifying a communication profile associated with a first network server, the communication profile including description information corresponding to a data compression format and a forward error correction toggle;
attempting, by the portable access device, to establish a communication link between the portable access device and the first network server using a communication channel that is selected by the portable access device based on the communication profile, a location of the portable access device with respect to the first network server, a desired quality of the communication link, and a cost of the communication link, wherein the communication channel is selected from the group consisting of: a local wireless LAN, a remote wireless LAN, a wireline LAN, and a Public Switched Telephone Network (PSTN), and attempting to establish the communication link includes using at least a portion of the description information;

capturing data received by the portable access device in a memory located in the portable access device in accordance with a failed attempt to establish the communication link;

establishing the communication link by using the selected communication channel when no user action is required to establish the communication link; and displaying a notification to instruct a user to perform a user action to establish the communication link when the user action is required to establish the communication link.

30. The computer-readable storage device of claim 29 wherein said step of identifying a communication profile associated with said network server further comprises the following steps:
searching an internal database for a communication profile associated with the first network server; and
retrieving said communication profile from the internal database.

31. The computer-readable storage device of claim 29 wherein said step of attempting to establish a communication link with said first network server is further comprised of the following steps:
configuring said portable access device to transmit using one of a plurality of communication channels, in accordance with said communication profile;
verifying the availability of said communication channel; and
initiating communication between said portable access device and said first network server along said communication channel.

32. The computer-readable storage device of claim 29 wherein attempting to establish a communication link comprises:
transmitting a first request from said portable access device to a local wireless LAN transceiver;
transmitting a second request from said portable access device to a remote wireless transceiver when a communication link cannot be established with said local wireless LAN transceiver; and
requesting a connection to a PSTN when a communication link cannot be established with said remote wireless transceiver.

33. The computer-readable storage device of claim 29 wherein identifying a communication profile further comprises:
searching an internal database of the portable access device for the communication profile;
transmitting from the portable access device to a second network server, a request to access the first network server when the communication profile cannot be found in the internal database; and
retrieving the communication profile from the second network server.

34. The computer-readable storage device of claim 33 wherein transmitting a request from a portable access device to the second network server comprises:
transmitting a first request from the portable access device to a local wireless LAN transceiver;
transmitting a second request from the portable access device to a remote wireless transceiver when a communication link cannot be established with the local wireless LAN transceiver; and connecting the portable access device to a PSTN when a communication link cannot be established with the remote wireless transceiver.

35. A computer-readable storage device containing instructions which, when executed by a processor, perform a method for accessing an information system comprising a portable access device and a plurality of network servers, the method comprising:
- identifying, by the portable access device, a communication profile associated with a first network server, wherein identifying a communication profile further comprises:
  - searching an internal database for the communication profile;
  - transmitting from the portable access device to a second network server, a request to access said first network server when said communication profile cannot be found in said internal database; and
  - retrieving the communication profile from said second network server, the communication profile including description information corresponding to a data compression format and a forward error correction toggle;
- attempting, by the portable access device, to establish a communication link between the portable access device and the first network server using one of a plurality of communication media, in accordance with the communication profile, a desired quality of the communication link, and a cost of the communication link, wherein the one of a plurality of communication media is selected from the group consisting of: a local wireless LAN, a remote wireless LAN, a wireline LAN, and a Public Switched Telephone Network (PSTN), and attempting to establish the communication link includes using at least a portion of the description information;
- capturing data in a memory location in accordance with a failed attempt to establish the communication link;
- establishing the communication link by using the selected communication channel when no user action is required to establish the communication link; and
- displaying a notification to instruct a user to perform a user action to establish the communication link when the user action is required to establish the communication link.

36. The computer-readable storage device of claim 35 wherein transmitting a request from the portable access device to the second network server comprises:
- transmitting a first request from the portable access device to a local wireless LAN transceiver;
- transmitting a second request from the portable access device to a remote wireless transceiver when a communication link cannot be established with the local wireless LAN transceiver; and
- connecting the portable access device to a PSTN when a communication link cannot be established with the remote wireless transceiver.

37. A computer-readable storage device containing instructions which, when executed by a processor, perform a method for accessing an information system comprising an access device and a plurality of network servers, the method comprising:
- transmitting from a portable access device to a first network server, a request to access a second network server;
- receiving said request at said first network server;
- identifying a communication profile associated with said second network server, the communication profile including description information corresponding to a data compression format and a forward error correction toggle;
- transmitting said communication profile to said portable access device;
- establishing a communication link between said portable access device and said second network server using a communication channel that is selected based on said communication profile, a location of the portable access device with respect to said second network server, a desired quality of the communication link, and a cost of the communication link, the communication link being established by using the selected communication channel when no user action is required to establish the communication link, wherein establishing the communication link includes using at least a portion of the description information; and
- displaying a notification to instruct a user to perform a user action to establish the communication link when the user action is required to establish the communication link.

38. The computer-readable storage device of claim 37 further comprising the step of configuring said portable access device to capture data in memory in accordance with a failed attempt to establish said communication link.

39. The computer-readable storage device of claim 37 wherein said step of transmitting from a portable access device to a first network server is further comprised of the following steps:
- transmitting a first request from a portable access device to a local wireless LAN transceiver;
- transmitting a second request from said portable access device to a remote wireless transceiver when a communication link cannot be established with said local wireless LAN transceiver; and
- connecting said portable access device to a PSTN when a communication link cannot be established with said remote wireless transceiver.

40. The computer-readable storage device of claim 37 wherein identifying a communication profile further comprises:
- accessing a central database; and
- retrieving a communication profile that corresponds to said second network server.

41. The computer-readable storage device of claim 37 wherein establishing a communication link comprises:
- configuring said portable access device to transmit using one of a plurality of communication channels in accordance with said communication profile;
- verifying the availability of a communication channel; and
- initiating communication between said profile access device and said second network server along said communication channel.

42. The computer-readable storage device of claim 37 wherein establishing a communication link comprises:
- transmitting a first request to a local wireless LAN transceiver;
- transmitting a second request to a remote wireless transceiver when a communication link cannot be established with said local wireless LAN transceiver; and
- connecting to a PSTN when a communication link cannot be established with said remote wireless transceiver.

* * * * *